United States Patent [19]
Chowdry et al.

[11] Patent Number: 5,717,976
[45] Date of Patent: Feb. 10, 1998

[54] STACK OF SHEETS AND METHOD OF ASSURING ORIENTATION

[75] Inventors: Arun Chowdry, Pittsford; Feraydoon S. Jamzadeh, Fairport, both of N.Y.

[73] Assignee: Eastman Kodak Company, Rochester, N.Y.

[21] Appl. No.: 631,589

[22] Filed: Apr. 12, 1996

Related U.S. Application Data

[60] Provisional application No. 60/003,268, Aug. 28, 1995.

[51] Int. Cl.$^6$ .................................................. G03G 15/00
[52] U.S. Cl. ........................ 399/45; 270/58.01; 271/145; 399/389
[58] Field of Search ............................. 399/389, 390, 399/45; 271/145, 241; 206/425, 449, 459.1, 459.5; 270/58.01, 58.03

[56] References Cited

U.S. PATENT DOCUMENTS

| | | | |
|---|---|---|---|
| 4,352,554 | 10/1982 | Kaye et al. | 355/40 |
| 4,426,290 | 1/1984 | Kaye et al. | 355/40 |
| 4,444,315 | 4/1984 | Gaskill et al. | 206/449 |
| 5,053,814 | 10/1991 | Takano et al. | 271/145 X |
| 5,067,835 | 11/1991 | Yamamoto et al. | 271/145 X |
| 5,085,417 | 2/1992 | Copham | 270/1.1 |
| 5,090,567 | 2/1992 | Boutet | 206/459.01 X |
| 5,196,868 | 3/1993 | No et al. | 346/134 |
| 5,243,394 | 9/1993 | Matsuno et al. | |
| 5,572,291 | 11/1996 | Moriguchi et al. | 399/390 |

*Primary Examiner*—Matthew S. Smith
*Attorney, Agent, or Firm*—Norman Rushefsky

[57] ABSTRACT

A stack of sheets, which sheets have different characteristics on their two sides, is marked on an edge of the stack with markings to prompt the user to properly orient the stack.

7 Claims, 1 Drawing Sheet

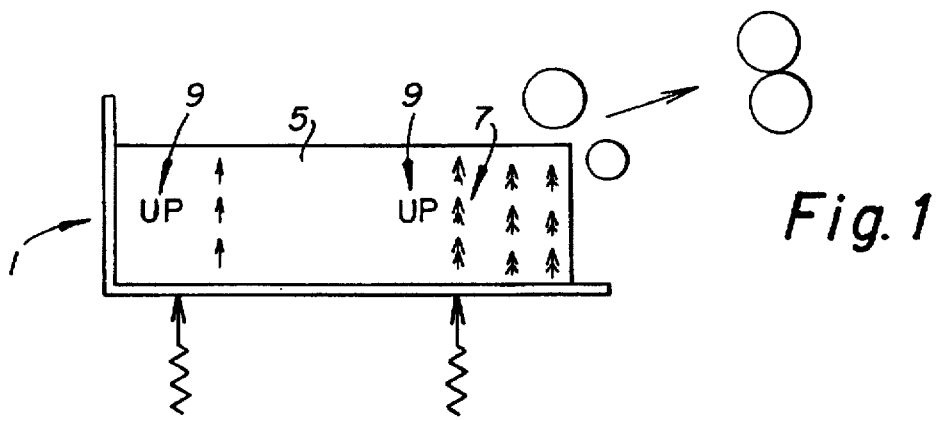
Fig. 1
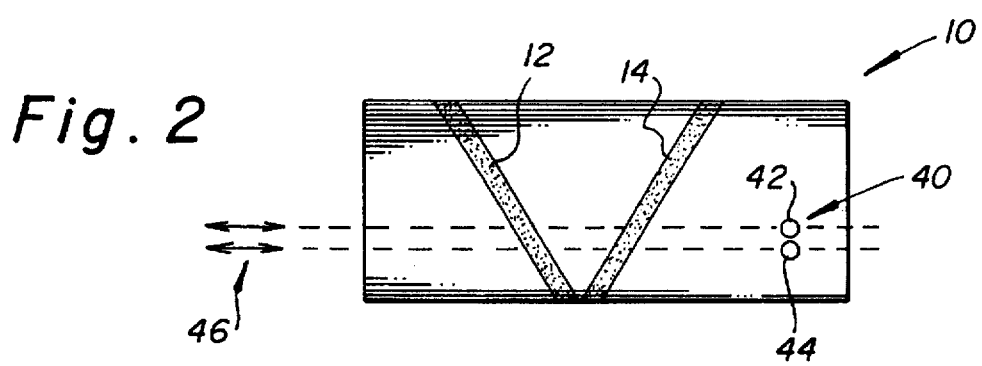
Fig. 2
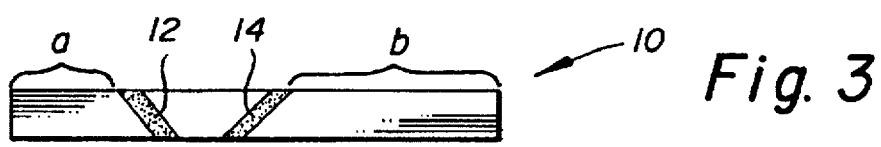
Fig. 3
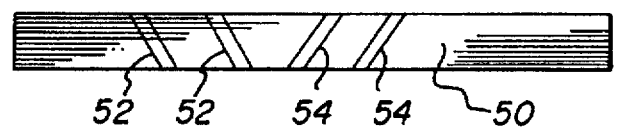
Fig. 4
Fig. 5
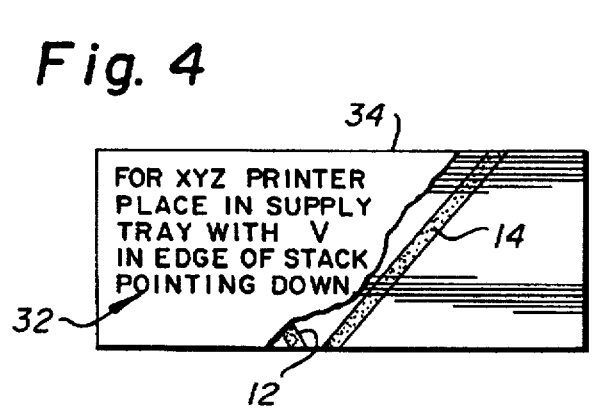

STACK OF SHEETS AND METHOD OF ASSURING ORIENTATION

CROSS REFERENCE TO RELATED APPLICATION

Reference is made to and priority claimed from U.S. Provisional application U.S. Ser. No. 60/003,268, filed 28 Aug. 1995, entitled STACK OF SHEETS AND METHOD OF ASSURING ORIENTATION.

This invention relates to methods using a stack of sheets. Although not limited thereto, it is particularly usable in image forming apparatus using sheets having sides with different characteristics.

Imaging devices which form very high quality images on a single side of a sheet commonly provide different surface treatment for the two sides rather than go to the expense of having an image receiving surface on both sides. It, thus, becomes critical to the operation of the image forming method that the sheets be oriented correctly in the image forming apparatus.

It is well known to optically detect such orientation when one side provides different optical characteristics than the other, for example, reflects more or less ultraviolet light. However, many sheets with different characteristics on their two sides are not so easily distinguished optically and many apparatus would prefer not to go to the expense of such a sensing device.

Another scheme used in the prior art to try to provide orientation of stacks is to place notches near a comer which may cooperate with a complimenting structure in the receiving paper sheet supply portion of an apparatus or cassette. It is not acceptable to have notches in some sheets, and the directions for using notches are not usually that easy to follow.

U.S. Pat. No. 5,085,417, Copham, granted Feb. 4, 1992, and U.S. Pat. No. 5,243,394, Matsuno et al, granted Sep. 7, 1993, are examples of the utilization of edge marks on a stack of sheets to distinguish jobs in a stack or to do quality checking on a manufactured stack.

SUMMARY OF THE INVENTION

It is an object of the invention to provide a method of assuring correct orientation of a stack of sheets having sides with different characteristics.

This and other objects are accomplished according to the invention by providing a visible marking or a visible incongruity such as an embossing on the edge of the stack indicative to a user of the proper orientation of the stack.

According to preferred embodiments, the edge marking can be self-explanatory, for example, with arrows and the words "up" or it can be understandable with the help of instructions, for example, instructions on the package in which the stack of sheets is supplied.

Although it is preferred that the markings be readable by a user for hand insertion of the sheets, they can also be made to be machine-readable so that a signal can be provided to the less sophisticated user that the sheets are not in the desired orientation.

According to another preferred embodiment, the markings can be in any of a variety of shapes which would maintain their information content even though the stack was incomplete. For example, an upright (or inverted) "V" would show orientation even though a few sheets were left in a stack or a few sheets were being used from the middle of the stack. Similarly, if the marking were off center, the orientation of a single sheet could be determined with proper instructions.

It is also an aspect of the invention to provide a stack of sheets, which stack has a visible marking or a visible incongruity on the edge indicative to a user of a proper orientation.

It is also an aspect of the invention to provide a package of sheets, which sheets are arranged in a stack having an orientation marking on an edge of the stack and suitable packaging for the stack having instructions to the user with respect to the marking.

BRIEF DESCRIPTION OF THE DRAWINGS

FIG. 1 is a side schematic of a supply tray containing a stack of sheets.

FIG. 2 is a side view of an alternative stack of sheets.

FIG. 3 is a side view of a portion of a stack of sheets.

FIG. 4 is a side schematic of a partially packaged stack of sheets with a cut away portion showing a portion of the stack that is unpackaged.

FIG. 5 is a side schematic of a cartridge for holding a stack of sheets.

DESCRIPTION OF THE PREFERRED EMBODIMENTS

According to FIG. 1, an imaging apparatus or other apparatus using a supply of asymmetrical sheets includes a supply tray 1 in which is positioned a stack 5 of sheets. Supply tray 1 is in an apparatus which uses sheets which vary in characteristics between their two sides and in which the variation is at least, to some extent, important to the operation of the machine and the method it carries out.

Many disciplines use sheets with varying characteristics from one side to another. For example, many graphic arts papers are smoother on one side than the other. Some electrophotographic papers contain layers that are heat softenable on one side. Even ordinary paper is not exactly symmetrical. For example, in some apparatus orientation of the "wire side" of a sheet to receive either a first or a second image in duplex operation provides better results than the reverse, although perhaps somewhat acceptable results are obtained with either orientation.

This invention is not limited to any one of these processes but is usable whenever a method or process prefers a particular orientation of a sheet fed from a stack of sheets.

Referring again to FIG. 1, stack 5 has edge markings 9 shown as the word "UP" in several places on the edge of the stack and a number of arrows 7 pointing in a particular direction toward one side of the sheets in the stack. Without other more specific directions, the operator is prompted by this edge marking to orient the sheets with the arrows pointing upward. Note also that with the arrows positioned at different places vertically in the stack, the orientation is still noticeable, even though only a partial stack is in the supply 1.

FIGS. 2 and 5 show somewhat simpler markings which may or may not be obvious to an unsophisticated operator. For example, in FIG. 2 a "V" is positioned across the edge of a stack 10. The V is made up of oppositely slanting black or other colored lines 12 and 14 which come closer together at the bottom, as shown.

Referring to FIG. 4, the stack shown in FIG. 2 is supplied in a wrapper 34 which includes instructions 32 that the stack should be placed in a supply tray with the V pointing down.

As illustrated in FIG. 3, even though a small portion of the stack is left at any time, the orientation of the V is still obvious to the operator and allows even a few sheets to be placed in the apparatus correctly. Further, if the V is made off center, even a single sheet can be placed correctly. For example, as shown in FIG. 3, a distance "a" is less than a distance "b" which allows the operator with only one sheet to note that the sheet itself is correctly oriented when the markings making up the V are to the left side of the supply tray.

Some of these markings, for example, the "V" shown in FIG. 2, are machine readable. As shown in FIG. 2, a sensing device 40 including sensors 42 and 44 are arranged to move along paths shown as dotted lines 46. If detector 42 encounters the V before 44 while moving from right to left from the position shown in FIG. 2, then the stack is correctly oriented. On the other hand, if detector 44 first encounters line 14, the stack is incorrectly oriented and a signal is sent to the operator to that effect.

Although a "V" is particularly attractive as a marking, the markings that could be used are infinite in number. Any marking which is not the same when inverted could be used with proper instructions on the package. Obviously, the more clear it is to the operator, the more useful that particular marking.

Many image forming devices, especially copiers and printers are loadable with cassettes or cartridges. A cassette or cartridge receiving such a stack could also have markings that would lead the operator to orient the stack properly. For example, as shown in FIG. 5, a cartridge 50 for receiving a set of sheets out of a stack comparable to stack 10 has lines molded in its side of similar angle as those forming the "V" on the stack. Multiple lines 52 and 54 are used in cartridge 50's sidewall to lead the operator to load the sheets correctly, whether they come from the top of stack 10 where the lines 12 and 14 are more separated, or the bottom of stack 10 where lines 12 and 14 are closer together. Note that the molded lines in the cartridge 50 are offset to the left to help the user orient even a single sheet.

The markings could also be made in an invisible colorant responsive to UV radiation, e.g., one that absorbs ultraviolet light and emits in the visible. This would allow a light in the paper supply with substantial UV content to make the lines visible and very noticeable to the user as the paper is being inserted while at the same time not being normally visible in the final product.

The invention has been described in detail with particular reference to a preferred embodiment thereof, but it will be understood that variations and modifications can be effected within the spirit and scope of the invention as described hereinabove and as defined in the appended claims.

We claim:

1. A method of assuring correct orientation of a stack of sheets, said stack having a first edge and an adjacent second edge and said sheets having opposite sides with different characteristics, said method comprising providing a colorant marking on the first edge of the stack indicative of proper orientation of the stack, the first edge of the stack being formed of respective first edges of the respective sheets in the stack, the respective first edges of the sheets each being straight without an irregularity and the colorant marking being for at least some sheets at different spacings from the second edge of the stack to provide an indication for a full stack and for a partial stack of proper up or down orientation of the stack.

2. The method according to claim 1 wherein the marking is in a colorant that is not visible in normal illumination but is visible when subjected to a particular illumination and wherein the method includes the step of viewing the first edge of the stack using the particular illumination as part of a process of orienting the stack of sheets.

3. The method according to claim 1 wherein the particular visible marking is in the shape of a V.

4. The method according to claim 1 further including the step of supplying the stack of sheets in a wrapper which instructs the operator with respect to utilizing the visible marking or visible incongruity in orienting the stack of sheets.

5. The method according to claim 1 further including the step of orienting the stack of sheets in a paper supply of an image forming apparatus in accordance with the visible marking on the first edge of the stack.

6. The method of claim 5 wherein each sheet has at least two spaced visible marking areas.

7. The method according to claim 1 further including electro-optically sensing the visible marking on the first edge of the stack located in an image forming apparatus to determine whether or not the orientation of the stack is correct.

* * * * *